(12) United States Patent
Park

(10) Patent No.: US 9,720,255 B2
(45) Date of Patent: Aug. 1, 2017

(54) APPARATUS FOR REMOVABLY ATTACHING OUTER LENSES TO GOGGLES

(71) Applicant: Soo An Park, Wonju-Si (KR)

(72) Inventor: Soo An Park, Wonju-Si (KR)

(73) Assignee: Spy Optic Inc., Carlsbad, CA (US)

( * ) Notice: Subject to any disclaimer, the term of this patent is extended or adjusted under 35 U.S.C. 154(b) by 0 days.

(21) Appl. No.: 14/531,662

(22) Filed: Nov. 3, 2014

(65) Prior Publication Data

US 2015/0124211 A1    May 7, 2015

Related U.S. Application Data

(60) Provisional application No. 61/900,710, filed on Nov. 6, 2013.

(51) Int. Cl.
*G02C 9/04* (2006.01)
*G02C 7/10* (2006.01)
*A61F 9/02* (2006.01)

(52) U.S. Cl.
CPC ............... *G02C 9/04* (2013.01); *A61F 9/025* (2013.01); *G02C 7/104* (2013.01)

(58) Field of Classification Search
CPC ...... G02C 7/104; G02C 9/04; G02C 2200/08; G02C 13/001
USPC ............ 351/47, 48, 57, 58; 2/426, 429, 434, 2/438, 439, 441, 443
See application file for complete search history.

(56) References Cited

U.S. PATENT DOCUMENTS

| | | | |
|---|---|---|---|
| 2,526,737 | A | 10/1950 | Farina |
| 3,056,140 | A | 10/1962 | Lindbolm |
| 3,298,031 | A | 1/1967 | Morgan |
| 3,363,262 | A | 1/1968 | Lindbolm |
| 3,377,626 | A | 4/1968 | Smith |
| 3,395,406 | A | 8/1968 | Smith |
| 3,505,680 | A | 4/1970 | Ring |
| 3,533,686 | A | 10/1970 | O'Shea |
| 3,754,298 | A | 8/1973 | Menil |
| 3,783,452 | A | 1/1974 | Benson et al. |
| 3,825,953 | A | 7/1974 | Hunter |

(Continued)

FOREIGN PATENT DOCUMENTS

| | | |
|---|---|---|
| CA | 2456476 | 3/2004 |
| DE | 2063092 | 7/1971 |

(Continued)

*Primary Examiner* — Ricky Mack
*Assistant Examiner* — Journey Sumlar
(74) *Attorney, Agent, or Firm* — Stetina Brunda Garred & Brucker

(57) ABSTRACT

An apparatus and method for removably attaching a lens to a pair of goggles. The lens has at its periphery a plurality of lens clips, and the goggles has on its frame a matching plurality of frame clips which are designed to attach to the lens clips. Attachment and unattachment may be achieved through actuation of a lens release mechanism. The apparatus allows for the rapid and easy replacement of lenses without necessitating a replacement of the remaining portion of the goggles, a feature which may allow a user to cost-effectively replace damaged or worn lenses, or to utilize a single pair of goggles in a multitude of activities or situations in which advantages may be conferred through or necessity may require the use of a type or style of lens having particular attributes.

20 Claims, 5 Drawing Sheets

(56) References Cited

U.S. PATENT DOCUMENTS

| | | |
|---|---|---|
| 3,896,496 A | 7/1975 | Leblanc et al. |
| 3,924,271 A | 12/1975 | Hirschmann, Jr. |
| 3,931,646 A | 1/1976 | Loughner |
| 3,945,044 A | 3/1976 | McGee et al. |
| 4,011,595 A | 3/1977 | Shields |
| 4,149,276 A | 4/1979 | Castro |
| 4,150,443 A | 4/1979 | McNeilly |
| 4,176,410 A | 12/1979 | Matthias |
| 4,264,987 A | 5/1981 | Runckel |
| 4,290,673 A | 9/1981 | Yamamoto |
| 4,317,240 A | 3/1982 | Angerman et al. |
| 4,425,669 A | 1/1984 | Grendol et al. |
| 4,428,081 A | 1/1984 | Smith |
| 4,443,893 A | 4/1984 | Yamamoto |
| 4,447,914 A | 5/1984 | Jannard |
| 4,455,689 A | 6/1984 | Boyer |
| 4,528,701 A | 7/1985 | Smith |
| 4,556,995 A | 12/1985 | Yamamoto |
| 4,571,748 A | 2/1986 | Carroll et al. |
| 4,603,442 A | 8/1986 | Barfield |
| 4,689,838 A | 9/1987 | Angermann |
| 4,707,863 A | 11/1987 | McNeal |
| 4,716,601 A | 1/1988 | McNeal |
| 4,868,929 A | 9/1989 | Curcio |
| 4,918,753 A | 4/1990 | Mermillod |
| 4,977,627 A | 12/1990 | Metcalfe et al. |
| 4,989,274 A | 2/1991 | Patelski et al. |
| 5,018,223 A | 5/1991 | Dawson et al. |
| 5,027,443 A | 7/1991 | Watkins |
| 5,046,200 A | 9/1991 | Feder |
| 5,056,163 A | 10/1991 | Chou |
| 5,069,541 A | 12/1991 | Holmes et al. |
| 5,093,940 A | 3/1992 | Nishiyama |
| 5,138,723 A | 8/1992 | Bolle |
| 5,182,817 A | 2/1993 | Branum |
| D334,758 S | 4/1993 | Reymondet et al. |
| 5,213,241 A | 5/1993 | Dewar et al. |
| 5,216,759 A | 6/1993 | Hewitt et al. |
| 5,339,119 A | 8/1994 | Gardner |
| 5,341,516 A | 8/1994 | Keim |
| D351,850 S | 10/1994 | Bolle |
| 5,363,512 A | 11/1994 | Grabos, Jr. et al. |
| 5,371,555 A | 12/1994 | Nagel |
| 5,406,340 A | 4/1995 | Hoff |
| D358,159 S | 5/1995 | Lai |
| 5,410,763 A | 5/1995 | Bolle |
| 5,421,037 A | 6/1995 | Schulze |
| 5,423,092 A | 6/1995 | Kawai |
| 5,452,480 A | 9/1995 | Ryden |
| 5,471,036 A | 11/1995 | Sperbeck |
| D367,664 S | 3/1996 | Simioni |
| 5,495,623 A | 3/1996 | Leonardi |
| 5,517,700 A | 5/1996 | Hoffman |
| D371,566 S | 7/1996 | Kolada et al. |
| 5,542,130 A | 8/1996 | Grabos et al. |
| 5,617,588 A | 4/1997 | Canavan et al. |
| 5,628,072 A | 5/1997 | Haslbeck |
| 5,636,388 A | 6/1997 | Hodges |
| 5,642,530 A | 7/1997 | Parks |
| 5,650,866 A | 7/1997 | Haslbeck |
| 5,652,965 A | 8/1997 | Crooks |
| 5,655,228 A | 8/1997 | Chiang |
| 5,657,106 A | 8/1997 | Herald, Jr. et al. |
| 5,657,493 A | 8/1997 | Ferrero et al. |
| 5,685,022 A | 11/1997 | Essman et al. |
| 5,687,428 A | 11/1997 | Yamamoto |
| 5,689,834 A | 11/1997 | Wilson |
| 5,711,035 A | 1/1998 | Haslbeck |
| D390,248 S | 2/1998 | Pranger |
| D391,594 S | 3/1998 | Huh |
| 5,768,716 A | 6/1998 | Porsche |
| 5,802,622 A | 9/1998 | Baharad et al. |
| 5,809,580 A | 9/1998 | Arnette |
| 5,815,235 A | 9/1998 | Runckel |
| 5,818,569 A | 10/1998 | Berent |
| 5,845,341 A | 12/1998 | Barthold et al. |
| D405,102 S | 2/1999 | Moritz et al. |
| 5,867,841 A | 2/1999 | Chiang |
| D408,431 S | 4/1999 | Simioni |
| 5,915,542 A | 6/1999 | Swiet |
| 5,927,281 A | 7/1999 | Monteleone et al. |
| 5,937,439 A | 8/1999 | Barthold et al. |
| 5,940,891 A | 8/1999 | Lane |
| D413,915 S | 9/1999 | Newcomb et al. |
| 5,966,745 A | 10/1999 | Schwartz et al. |
| 5,966,746 A | 10/1999 | Reedy et al. |
| 6,009,564 A | 1/2000 | Tackles et al. |
| 6,038,707 A | 3/2000 | Ryden et al. |
| 6,047,410 A | 4/2000 | Dondero |
| 6,049,917 A | 4/2000 | Ryden |
| 6,076,196 A | 6/2000 | Masumoto |
| D428,039 S | 7/2000 | Thixton |
| 6,092,243 A | 7/2000 | Wu et al. |
| 6,094,751 A | 8/2000 | Parks |
| 6,098,204 A | 8/2000 | Arnette |
| 6,098,205 A | 8/2000 | Schwartz et al. |
| 6,099,120 A | 8/2000 | De Lima |
| 6,105,177 A | 8/2000 | Paulson et al. |
| 6,119,276 A | 9/2000 | Newcomb et al. |
| 6,138,285 A | 10/2000 | Robrahn et al. |
| 6,138,286 A | 10/2000 | Robrahn et al. |
| D439,596 S | 3/2001 | Bolle |
| D442,206 S | 5/2001 | Meyerhoffer |
| 6,227,665 B1 | 5/2001 | Pernicka et al. |
| 6,253,387 B1 | 7/2001 | Yu |
| 6,282,727 B1 | 9/2001 | Lindahl |
| 6,282,728 B1 | 9/2001 | Baragar et al. |
| D450,833 S | 11/2001 | Olivieri |
| 6,321,391 B1 | 11/2001 | Basso |
| D457,545 S | 5/2002 | Khulusi |
| D457,551 S | 5/2002 | Khulusi |
| 6,415,452 B1 | 7/2002 | Watanabe et al. |
| 6,460,196 B2 | 10/2002 | Tsubooka et al. |
| 6,467,098 B1 | 10/2002 | Lee |
| D477,010 S | 7/2003 | Moritz et al. |
| 6,611,965 B1 | 9/2003 | Lee |
| 6,611,966 B1 | 9/2003 | Yamamoto et al. |
| 6,615,409 B2 | 9/2003 | Youmans et al. |
| 6,637,038 B1 | 10/2003 | Hussey |
| 6,665,885 B2 | 12/2003 | Masumoto |
| 6,691,324 B1 | 2/2004 | Nakamura |
| 6,704,944 B2 | 3/2004 | Kawaisnshi et al. |
| 6,715,157 B2 | 4/2004 | Mage |
| 6,718,561 B2 | 4/2004 | Dondero |
| 6,728,974 B2 | 5/2004 | Wadsworth |
| 6,732,382 B2 | 5/2004 | Dondero |
| 6,732,383 B2 | 5/2004 | Cleary et al. |
| 6,772,448 B1 | 8/2004 | Hockaday et al. |
| 6,826,785 B2 | 12/2004 | McNeal |
| D505,444 S | 5/2005 | Borlet et al. |
| 6,896,366 B2 | 5/2005 | Rice et al. |
| D509,236 S | 9/2005 | Sheldon |
| 6,952,841 B2 | 10/2005 | Schary et al. |
| 6,964,067 B1 | 11/2005 | Hartman |
| 6,986,169 B2 | 1/2006 | Nakamura |
| 7,039,959 B2 | 5/2006 | Dondero |
| 7,052,127 B2 | 5/2006 | Harrison |
| 7,058,992 B1 | 6/2006 | Ogonowsky |
| 7,062,797 B2 | 6/2006 | Khulusi |
| 7,073,208 B2 | 7/2006 | Penque, Jr. et al. |
| 7,096,514 B2 | 8/2006 | Khulusi |
| 7,100,215 B2 | 9/2006 | Shiue |
| 7,137,153 B2 | 11/2006 | Hussey |
| D537,098 S | 2/2007 | Sheldon et al. |
| 7,181,779 B2 | 2/2007 | Hussey |
| 7,192,137 B2 | 3/2007 | Ishibashi et al. |
| 7,200,875 B2 | 4/2007 | Dondero |
| D542,327 S | 5/2007 | Hsu |
| D542,829 S | 5/2007 | Hsu |
| D542,830 S | 5/2007 | Hsu |
| 7,260,850 B2 | 8/2007 | Ambuske et al. |
| D550,749 S | 9/2007 | Chiang |
| D552,662 S | 10/2007 | Woxing |
| 7,290,294 B2 | 11/2007 | Kita |

(56) References Cited

U.S. PATENT DOCUMENTS

| | | |
|---|---|---|
| D559,299 S | 1/2008 | Tabacchi |
| 7,343,631 B2 | 3/2008 | Liu |
| 7,356,854 B2 | 4/2008 | Sheldon |
| 7,370,374 B2 | 5/2008 | Penque, Jr. et al. |
| 7,404,217 B2 | 7/2008 | Polinelli et al. |
| 7,407,283 B2 | 8/2008 | Babineau |
| 7,510,279 B2 | 3/2009 | Van Atta et al. |
| D591,786 S | 5/2009 | Wang |
| 7,526,813 B2 | 5/2009 | Tominaga et al. |
| D598,040 S | 8/2009 | Sheldon et al. |
| D616,915 S | 6/2010 | Silveria et al. |
| D626,166 S | 10/2010 | Yang |
| D626,582 S | 11/2010 | Cheng |
| D640,724 S | 6/2011 | Goodman et al. |
| D649,178 S | 11/2011 | Moritz et al. |
| D649,577 S | 11/2011 | Goodman et al. |
| D669,113 S | 10/2012 | Sandor et al. |
| D675,244 S | 1/2013 | Orzeck et al. |
| D685,839 S | 7/2013 | Pearson et al. |
| D687,479 S | 8/2013 | Moritz et al. |
| D687,881 S | 8/2013 | Ginther et al. |
| D688,296 S | 8/2013 | Pearson et al. |
| D695,335 S | 12/2013 | Goodman et al. |
| 2002/0148034 A1 | 10/2002 | Lee |
| 2002/0157175 A1 | 10/2002 | Dondero |
| 2003/0110552 A1 | 6/2003 | Youmans et al. |
| 2005/0015862 A1* | 1/2005 | Dondero ............... A61B 5/0002 2/436 |
| 2005/0128426 A1 | 6/2005 | Shiue |
| 2006/0048289 A1 | 3/2006 | Shiue |
| 2006/0191062 A1 | 8/2006 | Matera |
| 2006/0272078 A1 | 12/2006 | Polinelli et al. |
| 2007/0033718 A1 | 2/2007 | Lin |
| 2008/0109949 A1 | 5/2008 | Kinsella |
| 2009/0019620 A1 | 1/2009 | Reed |
| 2009/0038059 A1 | 2/2009 | McNeal et al. |
| 2009/0122258 A1 | 5/2009 | Fielding, Jr. |
| 2014/0033408 A1* | 2/2014 | Currens ................. A61F 9/025 2/431 |

FOREIGN PATENT DOCUMENTS

| | | |
|---|---|---|
| DE | 2943472 | 5/1981 |
| EP | 0504518 | 8/1991 |
| EP | 1095577 | 7/2000 |

* cited by examiner

APPARATUS FOR REMOVABLY ATTACHING OUTER LENSES TO GOGGLES

CROSS-REFERENCE TO RELATED APPLICATIONS

This application claims the benefit of U.S. Provisional Application Ser. No. 61/900,710 filed Nov. 6, 2013, which is incorporated hereby reference in its entirety.

STATEMENT RE: FEDERALLY SPONSORED RESEARCH/DEVELOPMENT

Not applicable

BACKGROUND

1. Technical Field

The present disclosure relates generally to the attachment of outer lenses to goggles. More particularly, the present disclosure relates to an apparatus for removably attaching outer lenses to goggles in an easy and rapid fashion.

2. Related Art

In order to protect one's eyes during many sports or outdoor activities such as skiing, skydiving, paragliding, and so on, a person may wear goggles.

Typically, goggles are constructed of a frame, lenses which are fixedly mounted on the forward face of the frame, padding for comfort and absorbing sweat which is attached to the rear face of the frame, and a band for fixing the goggles to a user's head.

While generally all goggles share this basic design, it has been found that the experience of wearing goggles during certain sports or outdoor activities may be enhanced by wearing specialized or preferred lenses for that sport or activity. For example, variation in the colors of lenses may affect a wearer's perception of the brightness and contrast of their environment, as well as a wearer's depth perception and ability to perceive certain colors.

Additionally, during certain sports or outdoor activities, it is common that the lenses on a pair of goggles may become damaged, such as by becoming cracked, scratched, or crazed.

Thus, a wearer who owns a pair of goggles with integrated lenses, but desires to wear different lenses on their goggles, or to replace damaged lenses on their goggles, is required to purchase and adjust to an entirely new pair of goggles, or take the goggles to the manufacturer or a specialist for replacement of lenses.

Thus, there is a need in the art for an improved goggle. Various aspects of the present invention address this need, as will be explained in more detail below.

BRIEF SUMMARY

To solve these and other problems, an apparatus is contemplated which provides for removably attaching outer lenses to goggles in a way that allows easy and rapid replacement of a lens by the wearer. Thus, a user may rapidly and inexpensively replace a damaged lens, or swap from one lens to another to suit their particular needs at any given moment, without requiring the user to obtain or store a separate pair of goggles.

According to one embodiment, the apparatus includes a frame and a lens rim attachable to the frame. A plurality of lens clips are disposed on the lens rim, and a plurality of frame clips are disposed on the frame. Each lens is configured to attach to a respective frame clip, and when every lens clip is attached to its respective frame clip, the lens rim is attached to the frame. The frame clips include a movably attached frame clip that is movable relative to the frame between a first position and a second position. A lens release mechanism is coupled to the frame and is actuated to cause the movably attached frame clip to move between the first position and the second position. When the movably attached frame clip is moved to the second position, a lens clip attached to that movably attached frame clip becomes unattached.

The plurality of frame clips includes a fixedly attached frame clip. The fixedly attached frame clip and the movably attached frame clip are be disposed on opposing portions of the frame. Specifically, the fixedly attached frame clip and the movably attached frame clip are situated proximal to opposing temple regions of the frame.

The movably attached frame clip is biased towards the first position. Such a bias results in the movably attached frame clip returning to the first position after the actuation of the lens release mechanism causes the movably attached frame clip to move to the second position.

Each of the plurality of frame clips comprises hook members. The frame also comprises a forward facing surface surrounding a lens rim slot which is sized and dimensioned to accept complementary placement of a lens rim. The frame may be configured so that when the lens rim is complementarily placed in the lens rim slot, the forward facing surface of the frame is substantially flush with the lens rim. The lens release mechanism may be, for example, a button.

An attached lens rim may be removed from the frame by actuation of the lens release mechanism. The removal may also include the additional step of moving the lens rim away from the frame.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

According to various aspects of the present invention, an apparatus and related method for removably attaching a lens to a frame is contemplated, which utilizes a frame with a plurality of frame clips which are configured to selectively attach to respective ones of a plurality of lens clips situated on a lens rim. The frame clips include at least one frame clip movably attached to the frame and movable in response to actuation of a lens release mechanism. When actuated, the lens release mechanism may cause a movable frame clip to move, allowing the lens clip to become attached or unattached to or from the frame clip. It is additionally contemplated that certain frame clips may be fixedly attached to the frame. The frame clips may have a hook member configured to attach to lens clips which have a corresponding eyelet member.

Figure 1:
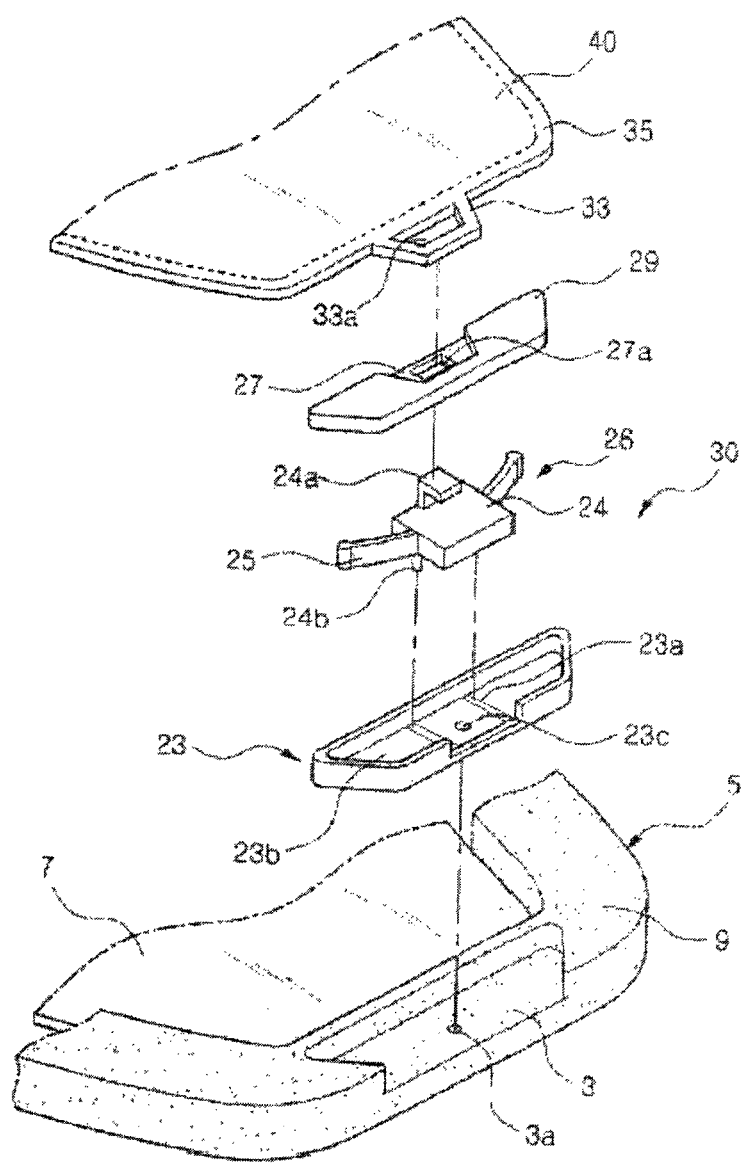
FIG. 1 is a partial exploded perspective view of one embodiment of a lens attachment apparatus.

Referring now to the figures, and more particularly to FIG. 1, an apparatus according to an exemplary embodiment of the present invention is shown. The embodiment includes a frame 5 having a frame clip slot 3, a lens rim slot 7, and a forward facing surface 9. The frame 5 may be any style or construction of frame typically used in a pair of goggles or other eyewear, and it may be seen that the frame 5 may be formed, sized, and configured according to known methods or ways of forming, sizing, and configuring a frame.

The frame clip slot 3 is, in the exemplary embodiment, an opening portion extending into the forward facing surface 9 at the periphery of a frame 5 to form a cavity. The frame clip slot 3 does not extend through the entire frame 5, but rather terminates to create a surface. The frame clip slot 3 of the exemplary embodiment has a dovetail configuration in which there are peripheral walls on three sides of the frame clip slot 3, with the fourth side being open to the edge of the frame 5. In the dovetail configuration, the frame clip slot 3 is wider towards the inside of the frame 5, and narrows progressively towards the periphery of the frame 5. It may be seen, however, that in other embodiments, frame clip slot 3 may be differently sized and configured differently. It may be seen that the frame clip slot 3 may be cut into the surface portion 9 of frame 5, or may be formed concurrently with the frame 5 as part of a molding process.

The lens rim slot 7 is, in the exemplary embodiment, an opening portion extending into the forward facing surface 9, at the interior periphery of forward facing surface 9 of frame 5 to form a cavity. The lens rim slot 7 preferably does not extend through the entire frame 5, but rather terminates to create a surface. In one embodiment, the lens rim slot 7 extends about the entire forward facing surface 9 of frame 5. In other embodiments, however, it may be seen that there may be multiple lens rim slots 7 when multiple lenses are used with a pair of goggles. It may be seen that the lens rim slot 7 may be cut into the surface portion 9 of frame 5, or may be formed concurrently with the frame 5 as part of a molding process.

The frame 5 may have disposed proximal to the frame clip slot 3 a frame clip engagement portion 3a for attachment of a frame clip 30. In the exemplary embodiment, the frame clip engagement portion 3a is an opening sized and configured for placement of a rivet through the opening. However, it may be seen that in other embodiments, frame clip engagement portion 3a may include any type of fastener suitable for fastening together components used in the construction of goggles, and may include mechanical fasteners which include, for example but without limitation, bolts, clamps, nails, rivets, screws, or adhesives.

The exemplary embodiment also includes a frame clip assembly 30. In one exemplary embodiment, frame clip assembly 30 has a lower frame clip housing 23, a frame clip 26, and an upper frame clip housing 29.

In the exemplary embodiment, lower frame clip housing 23 is sized and configured to fit within the frame clip slot 3 of the frame 5, having a lower surface and four walls extending upward so as to be shaped in a similar dovetail configuration as frame clip slot 3. The exterior wall is placed in alignment with the periphery of the frame 5, and has a cutout portion. The lower frame clip housing 23 includes a frame clip groove 23a, a frame clip cavity portion 23b, and a lower frame clip fastener 23c. The frame clip groove 23a is, in the exemplary embodiment, two grooves in the lower surface of lower frame clip housing extending from the wall facing the interior of the frame 5 to the cutout portion of the exterior wall. The frame clip groove 23a is in a slidingly engagable relation with the frame clip 26, which allows frame clip 26 to move parallel to the path of frame clip groove 23a. It may be seen that in other embodiments, however, frame clip groove 23a may be, for example but without limitation, a ridge, slide or track.

In the exemplary embodiment, the frame clip cavity portion 23b is an opening portion of the lower frame clip housing 23 sized and dimensioned to accept placement of the frame 26. The frame clip cavity portion 23b has a similar dovetail configuration as the lower frame clip housing 23, and is defined by the interior wall, the two side walls, and the exterior wall having a cutout portion.

In the exemplary embodiment, the lower frame clip engagement portion 23c is an opening portion placed coaxially with the frame clip engagement portion 3a, through which a rivet may be placed to fasten the frame clip assembly 30 to the frame 5. However, it may be seen that in other embodiments, lower frame clip may be any type of fastener suitable for fastening together components used in the construction of goggles, and may be mechanical fasteners which include, for example but without limitation, bolts, clamps, nails, rivets, screws, or adhesives.

In the exemplary embodiment, frame clip 26 is a member placed within the lower frame clip housing 23 having a lens release mechanism 24, a hook member 24a, a frame clip guide 24b, and a biasing member 25.

Lens release mechanism 24, in the exemplary embodiment, is a button connected to the frame clip 26 which, when the frame clip 26 is placed in the lower frame clip housing 23, extends through the cutout portion of the exterior wall of the frame clip housing 23 so as to be accessible to a user for actuation. In the case of the exemplary embodiment, actuation consists of pressing the lens release mechanism 24 to move the frame clip 26 relative to the frame 5 and the frame clip assembly 30 between a first position and a second position. However, it may be seen that in other embodiments, lens release mechanism 24 may be any mechanism which may be actuated to cause frame clip 26 to move relative to the frame 5 between a first position and a second position. The lens release mechanism 24 may be, for example but without limitation, a lever, knob or switch.

In the exemplary embodiment, hook member 24a is a portion of the frame clip 26 extending in a direction outward from the forward facing surface 9 of the frame 5, consisting of a vertical portion and a horizontal portion, and configured to attach to an eyelet in a hook-and-eyelet fastening scheme. Hook member 24a may be seen to traverse along a path parallel to frame clip groove 23a in response to actuation of the lens release mechanism 24 between a first position and a second position. In other embodiments, however, hook member 24a may be any fastener which may be configured to be attached and unattached from another fastener through actuation of lens release member 24. For example but without limitation, hook member 24a may be clamps, latches, couplings, or locks.

Frame clip guide 24b, in the exemplary embodiment, consists of pins sized to fit within and slidingly engage with frame clip groove 23a so that frame clip 26 traverses parallel to frame clip groove 23a when lens release mechanism 24 is actuated. In other embodiments, however, frame clip guide 24b may be, for example but without limitation, prongs, pegs, rods, slides or ridges.

Biasing member 25 may place tension on frame clip 26 and may cause frame clip 26 to return to a first position following movement to a second position by actuation of a lens release mechanism 24. In the exemplary embodiment, biasing member 25 includes two prongs extending outward from frame clip 26, with distal portions of both prongs being enlarged and configured to impinge upon the interior wall of lower frame clip housing 23 when frame clip 26 is in both the first position and the second position, so as to bias frame clip 26 to the first position. When lens release mechanism 24 is actuated, causing frame clip 26 to traverse to the second position, the two prongs of biasing member 25 may be seen to traverse outward along the inner wall of lower frame clip housing member 23 to maintain and increase the biasing force on frame clip 26. It may be seen that, in other embodiments, biasing member 25 may be anything calculated to result in bias or tension on frame clip 26, including but not limited to springs, elastics or resiliently biased materials.

Upper frame clip housing 29 may include, in the exemplary embodiment, a lens clip slot 27 and an upper frame clip opening portion 27a. Upper frame clip housing 29 may be sized and configured to retain frame clip 26 within the frame clip cavity portion 23b of the lower frame clip housing 23. In the exemplary embodiment, upper frame clip housing 29 has the same general dovetail shape and size as lower frame clip housing 23, and is placed against lower frame clip housing 23 to house frame clip 26.

Lens clip slot 27, in the exemplary embodiment, is an opening portion in upper frame clip housing 29 resulting in a cavity in a dovetail configuration terminating in a lower surface not extending all the way through upper frame clip housing 29. The interior portion of the cavity of lens clip slot 7 is wider than the exterior portion, and is open and aligned with a wall of lens rim slot 7.

The lower surface of lens clip slot 27, in the exemplary embodiment, has an frame clip opening portion 27a. Frame clip opening portion 27a is sized and configured to allow the passage therethrough of hook member 24a. Frame clip opening portion 27a, in the exemplary embodiment, is a rectangular defined opening extending entirely through the upper frame clip housing 29, with the sides of the rectangular defined opening parallel to the frame clip groove 23a being of a length equal to or longer than the length traveled by the frame clip 26 between the first position and second position, and the sides of the rectangular defined opening transverse to the frame clip groove 23a being of a length equal to or wider than the vertical portion of the hook member 24a, to allow relatively unimpaired movement of the hook member 24a within the frame clip opening portion 27a when the frame clip 26 is moved between the first position and the second position by actuation of the lens release mechanism 24.

The apparatus may also comprise a lens rim 35 at the periphery of a lens 40, and one or more lens clips 33. In the exemplary embodiment, lens clip 33 includes an eyelet member 33a for attachment to a hook member 24a of a frame clip 26. However, it may also be seen that in other embodiments, other mechanisms for attachment of a lens clip 33 to a frame clip 26 may be utilized, and that such mechanisms fall within the scope of the present disclosure. It may also be seen that lens 40 may be any type of lens used or usable in the construction of goggles or other eyewear, and lens rim 35 may encompass the rim or periphery of any such lens 40, so long as a lens clip 33 for attachment to frame clip 26 is present. In an exemplary embodiment, lens rim 35 is a separate element disposed on the perimeter of the lens 40. However, it may be seen that in other embodiments, lens rim 35 may be, for example but without limitation, the material of the lens 40 itself, or may be disposed in locations other than the perimeter of the lens 40.

Figure 5:
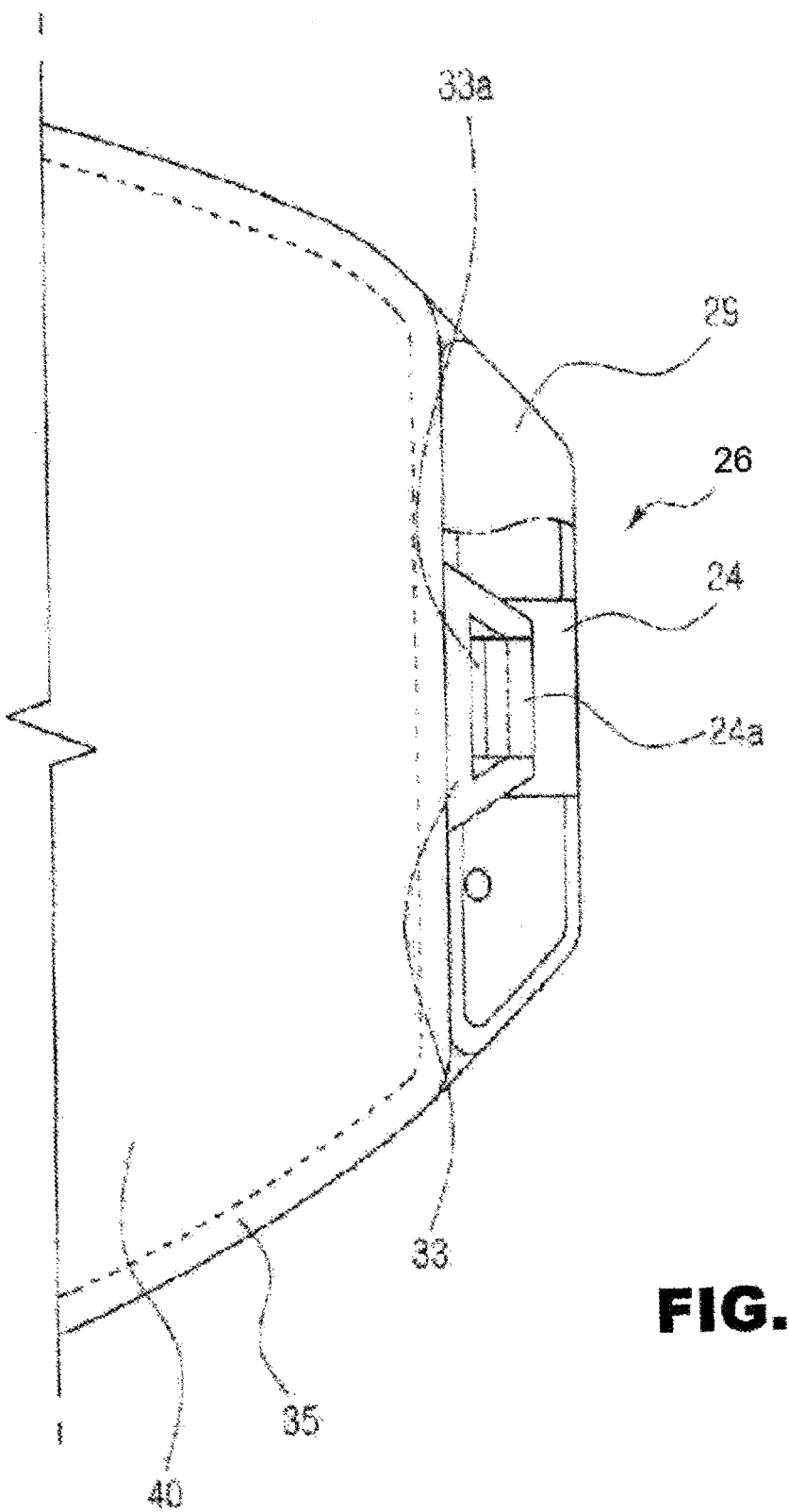
FIG. 5 is a partial front view of the lens rim of one embodiment of lens attachment apparatus with a fixed frame clip.

In another embodiment, shown in FIG. 5, frame clip 26 may be a fixedly attached frame clip. In such an embodiment, hook member 24a attached to the frame 5 may be all that is required to comprise the frame clip 26, and the remaining portions of frame clip apparatus 30 may be unnecessary. It may be seen that certain embodiments of the apparatus may have various combinations of fixedly attached and movably attached frame clips 26. For example, one particular embodiment may include one fixedly attached frame clip 26 and one movably attached frame clip 26 for retaining a lens to a pair of goggles. Other embodiments may include those which utilize two or more movably attached frame clips 26, or other numbers of fixedly attached and movably attached frame clips 26.

Lens rim slot 7 is, in the exemplary embodiment, sized and configured to accept the placement of lens rim 35 therein. In such a fashion, it may be seen that in certain embodiments, the forward facing surface of frame 5 may be configured to be, for example, substantially flush with lens rim 35 when lens rim 35 is placed in the lens rim slot 7. Such a configuration may have certain advantages in, for example, improving airflow over the goggles or preventing lens 40 from easily becoming dislodged or shifted. Such an arrangement may also provide an aesthetic benefit. However, it may also be seen that embodiments in which the lens rim 35 is not substantially flush with the forward facing surface of the frame 5 are within the scope of the present disclosure. The same considerations of airflow, damage resistance, and aesthetic appeal may also be taken into account with respect to the placement of lens clip 33 into lens clip slot 27 during attachment to frame clip 26, and the placement of frame clip assembly 30 into frame clip slot 3, and it may be seen that various arrangements of components of the apparatus may accentuate certain of the above discussed advantages as well as other advantages which may be realized, and that such arrangements fall within the scope of the present disclosure.

Figure 2:
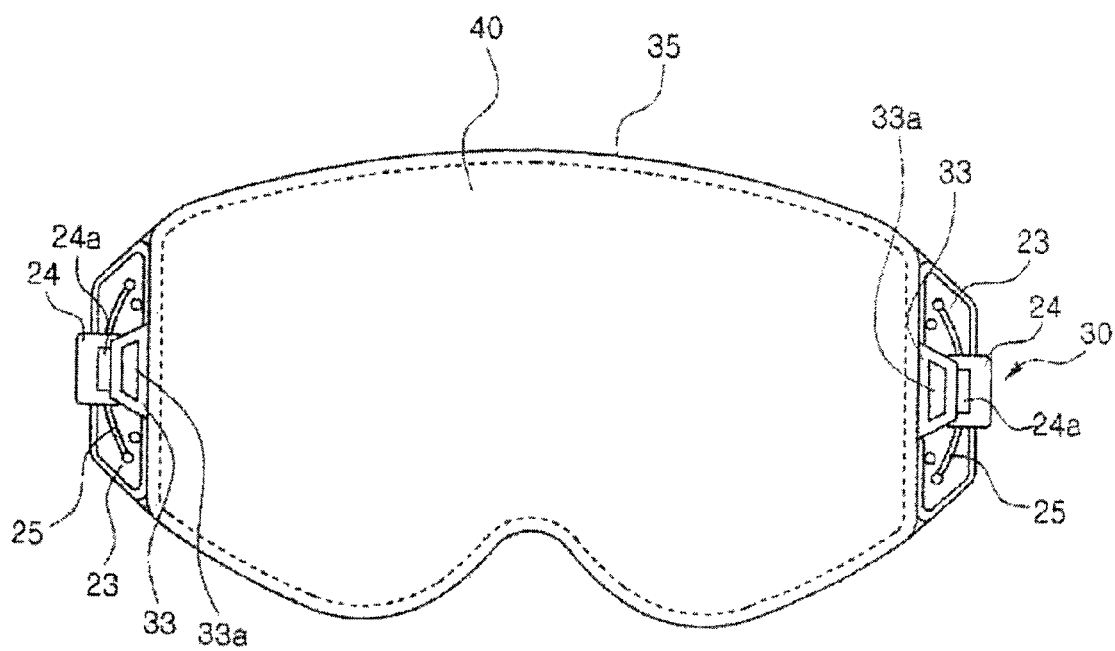
FIG. 2 is a front view of the lens and the frame of one embodiment of the lens attachment apparatus.

Referring now to FIG. 2, a front view of an exemplary embodiment is shown in which two frame clips assemblies 30 and two lens clips 33 are utilized. In such an embodiment, it may be seen that the frame clips assemblies 30 are situated at opposing sides of the frame 5. Such a placement may have the advantage of providing only a few points of attachment for ease of detachment, but also may provide adequately secure attachment of the lens 40 to the frame 5 in the event of impact or shock which may occur during the typical course of use of a pair of goggles. Additionally, the placement of opposing frame clip assemblies 30 at the temple regions of the frame 5, which are the regions of the frame 5 adjacent to the temples of a typical wearer when worn on the head and over the eyes, may provide enhanced visibility and ease of access to lens release mechanism 24.

Figure 3:
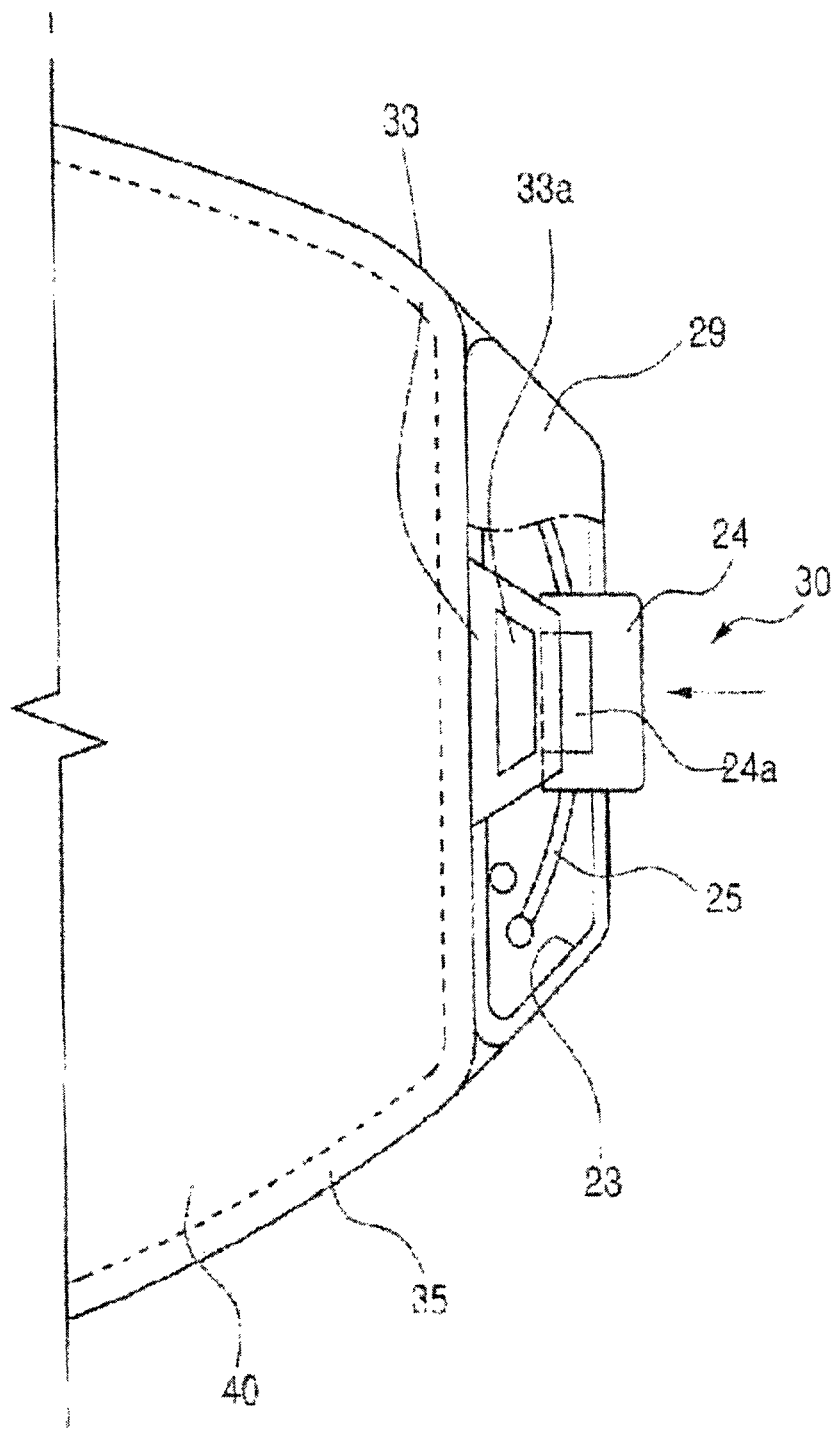
FIG. 3 is a partial front view of the lens rim of one embodiment of the lens attachment apparatus, unattached from the frame.

Referring now to FIG. 3, a front view of an exemplary embodiment having a movably attached frame clip 26 is shown, in which a lens clip 33 is ready for attachment to movably attached frame clip 26. It may be seen that when the lens release mechanism 24 is actuated, the frame clip 26 traverses, causing the hook member 24a to move from a first position to a second position in order to catch and engage eyelet member 33a. The biasing action of biasing member 25 may then return hook member 24a to the first position, causing the attachment of hook member 24a of frame clip 26 to eyelet member 33a of lens clip 33.

Figure 4:
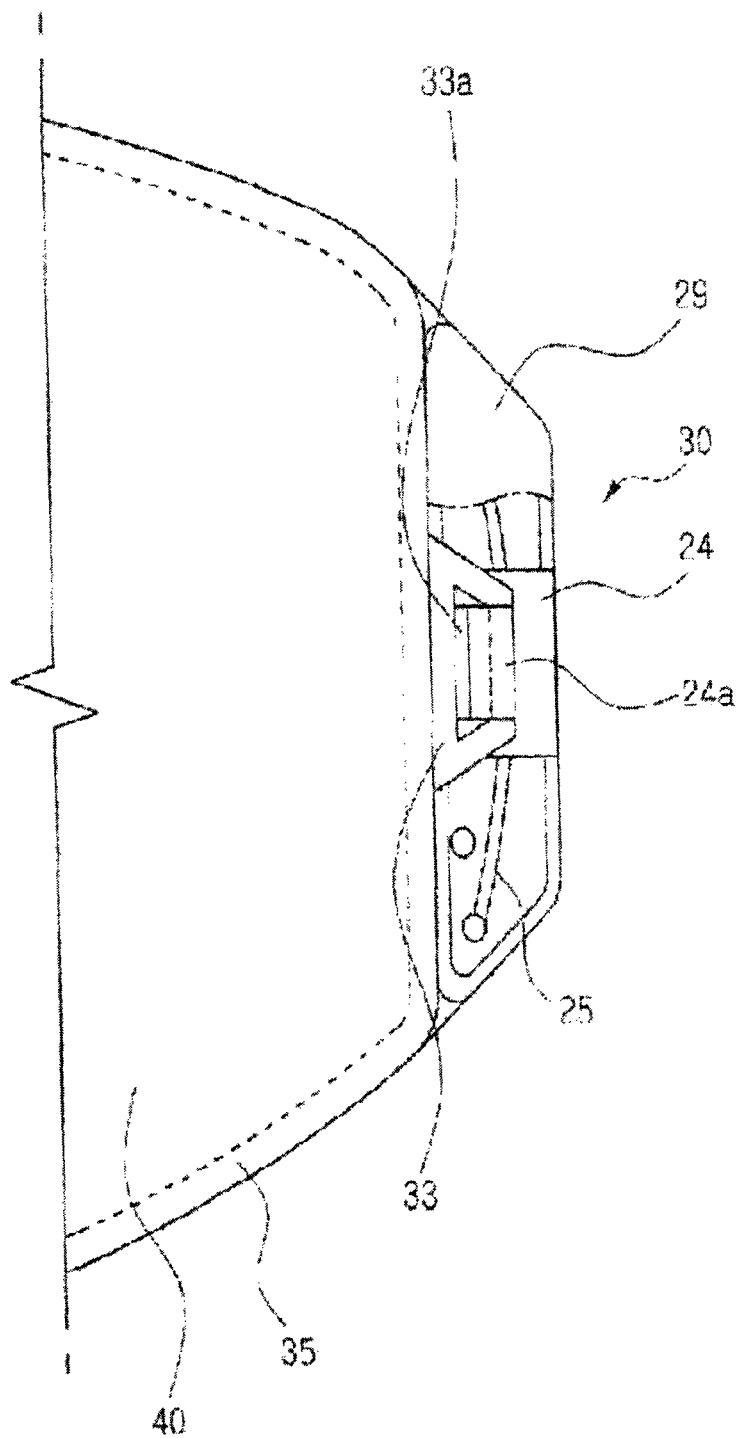
FIG. 4 is a partial front view of the lens rim of one embodiment of the lens attachment apparatus, attached to the frame.

Referring now to FIG. 4, a front view of an exemplary embodiment in which lens clip 33 is engaged with frame clip 26 is shown. It may be seen that hook member 24a of frame clip 26 is attached to eyelet member 33a of lens clip 33, and that the biasing action of biasing member 25 prevents unattachment of the two. It may also be seen that in order to unattach hook member 24a of frame clip 30 from eyelet member 33a of lens clip 33, lens release mechanism 24 may be actuated so as to cause frame clip 26 to traverse, releasing eyelet member 33a from hook member 24a. The lens rim 35 may then be removed from the frame 5 by, for example, lifting it out of the lens rim slot 7 by a user grasping a portion of the lens 40 or lens rim 35 and moving the lens 40 away from the frame. Additional elements operatively attached to the lens 40 may be provided for ease of grasping to aid in such removal of the lens 40 from the frame 5.

With the primary structural features of the apparatus described above, the following discussion describes usage of the apparatus according to aspects of the present invention. In the exemplary embodiment, a lens 40 may be attached to a frame 5 having two movably attached frame clips 26 by the user placing a lens rim 35 into a lens rim slot 7 and aligning the lens clips 33 in the lens clip slots 27. The user may then actuate the lens release mechanisms 24, causing each of the frame clips 26 to traverse along the path of frame clip grooves 23a from the first position to the second position. In the second position, the hook member 24a of the lens clip 26 is aligned within the eyelet member 33a of the lens clip 33. Following release of the lens release mechanism, the biasing member 25 causes the lens clip 26 to return from the second position to the first position along the path of lens clip groove 23a, causing the hook members 24a of the frame clips 26 to catch and retain eyelet members 33a of the lens clips 33, resulting in attachments of the frame clips 26 to lens clips 33, and thus attachment of the lens rim 35 to the frame 5.

The lens may then be unattached from the frame 5, in the exemplary embodiment having two movably attached frame clips, by the user actuating the lens release mechanisms 24, causing the frame clips 26 to move from the first position to the second position along the frame clip groove 23a. This causes the hook members 24a of the frame clips 26 to release the eyelet members 33a of the lens clips 33 and align within the eyelet members. The lens 40 is then unattached from the frame 5 and may then be manually removed from the lens slot 7.

In another embodiment in which one movably attached frame clip 26 and one fixedly attached frame clip 26 is used, the lens 40 may be attached and detached by the actuation of a single lens release mechanism 24. To attach the lens 40 to the frame 5, the eyelet member 33a of one lens clip 33 may be manually engaged with the fixed frame clip 26, and another lens clip 33 then may be aligned with the movably attached frame clip 26. The lens release mechanism 24 may then be actuated to attach the movably attached frame clip 26 to the aligned lens clip 33 in the same fashion as described above in the exemplary embodiment. To detach the lens 40 from the frame in this embodiment, the lens release mechanism 24 may be actuated as described above in the exemplary embodiment, and the unattached lens clip 33 may then be manually unaligned from the movably attached frame clip by the user. The fixedly attached frame clip may then be manually detached from the other lens clip 33 by the user.

It may thus be seen that the apparatus as described may allow for the rapid replacement of a lens 40. This may be useful, for example, when a lens 40 is damaged and needs to be replaced, allowing easy repair by the user, circumventing the purchase of a new frame 5. Additionally, a user may desire to utilize a variety of lenses 40 with a single pair of goggles. Such lenses 40 may be, for example, lenses which have different colors or tinting, prescription lenses, or lenses with other desired styles or optical properties.

The above description is given by way of example, and not limitation. Given the above disclosure, one skilled in the art could devise variations that are within the scope and spirit of the invention disclosed herein, including various ways of configuring or attaching the frame clip 26 and the lens clip 33. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An apparatus for removably attaching a lens to goggles, the apparatus comprising:
   a frame;
   a lens rim attachable to the frame;
   a plurality of lens clips disposed on the lens rim;
   a plurality of frame clips disposed on the frame and configured to attach to respective ones of the lens clips, the plurality of frame clips including a movably attached frame clip movable relative to the frame between a first position and a second position;
   a biasing element mounted on the movably attached frame clip; and
   a lens release mechanism coupled to the frame and actuatable to cause the moveably attached frame clip to move between the first position and the second position;
   wherein when each of the plurality of frame clips are attached to each of the respective ones of the plurality of lens clips, the lens rim is attached to the frame;
   wherein when the movably attached frame clip is in the second position, a respective one of the lens clip attached to the movably attached frame clip becomes unattached.

2. The apparatus of claim 1, wherein the plurality of frame clips includes a fixedly attached frame clip fixed to the frame.

3. The apparatus of claim 2, wherein the fixedly attached frame clip and the movably attached frame clip are oppositely disposed on the frame.

4. The apparatus of claim 3, wherein the fixedly attached frame clip and the movably attached frame clip are situated proximal to opposing temple regions of the frame.

5. The apparatus of claim 1, wherein the movably attached frame clip is biased towards the first position.

6. The apparatus of claim 5, wherein the movably attached frame clip is configured to return to the first position after being moved to the second position by actuation of the lens release mechanism.

7. The apparatus of claim 1, wherein each of the plurality of frame clips comprise hook members.

8. The apparatus of claim 1, wherein the lens release mechanism is a button.

9. The apparatus of claim 1, wherein the frame further comprises a forward facing surface surrounding a lens rim slot, the lens rim slot being sized and dimensioned to accept complementary placement of a lens rim.

10. The apparatus of claim 9, wherein when a lens rim is complimentary placed in a lens rim slot, the forward facing surface of the frame is flush with the lens rim.

11. An apparatus for removably attaching a lens to goggles, comprising:
- a frame;
- a lens rim attachable to the frame;
- two lens clips disposed on the lens rim;
- two opposed frame clips disposed on the frame and configured to attach to respective ones of the lens clips, one frame clip being movably attached to the frame and movable relative to the frame between a first position and a second position, and one frame clip being fixedly attached to the frame;
- a biasing element mounted on the movably attached frame clip; and
- a button coupled to the frame and actuatable to cause the moveably attached frame clip to move between the first position and the second position;
- wherein when the two frame clips are attached to the respective two lens clips, the lens rim is attached to the frame;
- wherein when the movably attached frame clip is in the first position, the respective one of the lens clip attached to the movably attached frame clip remains attached;
- wherein when the movably attached frame clip is in the second position, the respective one of the lens clip attached to the movably attached frame clip becomes unattached.

12. The apparatus of claim 11, wherein the frame clips are situated proximal to opposing temple regions of the external portion of the frame.

13. The apparatus of claim 11, wherein the movably attached frame clip is biased towards the first position.

14. The apparatus of claim 13, wherein the movably attached frame clip is configured to return to the first position after being moved to the second position by actuation of the lens release mechanism.

15. The apparatus of claim 11, wherein the frame further comprises a forward facing surface surrounding a lens rim slot, wherein when a lens rim is complimentary placed in the lens rim slot, the forward facing surface of the frame is flush with the lens rim.

16. The apparatus of claim 11, further comprising a lens release handle operatively attached to the lens rim.

17. The apparatus of claim 11, wherein the frame comprises a forward facing surface surrounding a lens rim slot, the lens rim slot being sized and dimensioned to accept complementary placement of a lens rim.

18. The apparatus of claim 17, wherein when a lens rim is complimentary placed in a lens rim slot, the forward facing surface of the frame is flush with the lens rim.

19. A method of detaching a removably attached lens from goggles, comprising the steps of:
- Providing:
  - a frame;
  - a lens rim attachable to the frame;
  - a plurality of lens clips disposed on the lens rim;
  - a plurality of frame clips disposed on the frame and configured to attach to respective ones of the lens clips, the plurality of frame clips including a movably attached frame clip comprising a biasing element movable relative to the frame between a first position and a second position; and
  - a lens release mechanism coupled to the frame and actuatable to cause the moveably attached frame clip to move between the first position and the second position;
  - wherein when each of the plurality of frame clips are attached to each of the respective ones of the plurality of lens clips, the lens rim is attached to the frame;
  - wherein when the movably attached frame clip is in the second position, a respective one of the lens clip attached to the movably attached frame clip becomes unattached;
- actuating the lens release mechanism to cause a lens clip to become unattached from a frame clip.

20. The method of claim 19, wherein the actuating step further comprises moving the lens rim away from the frame.

* * * * *